(12) United States Patent
Blake et al.

(10) Patent No.: US 10,883,643 B2
(45) Date of Patent: Jan. 5, 2021

(54) FLUID CONNECTION SYSTEM AND PRODUCTION METHOD

(71) Applicant: SARTORIUS STEDIM FMT SAS, Aubagne (FR)

(72) Inventors: Florian Blake, La Ciotat (FR); Isabelle Gay, Peypin (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 217 days.

(21) Appl. No.: 15/528,298

(22) PCT Filed: Nov. 20, 2015

(86) PCT No.: PCT/FR2015/053156
§ 371 (c)(1),
(2) Date: May 19, 2017

(87) PCT Pub. No.: WO2016/079451
PCT Pub. Date: May 26, 2016

(65) Prior Publication Data
US 2017/0314719 A1    Nov. 2, 2017

(30) Foreign Application Priority Data
Nov. 21, 2014 (FR) ...................... 14 61311

(51) Int. Cl.
*F16L 13/00* (2006.01)
*F16L 47/22* (2006.01)
(Continued)

(52) U.S. Cl.
CPC ............ *F16L 47/22* (2013.01); *A61M 39/00* (2013.01); *A61M 39/10* (2013.01);
(Continued)

(58) Field of Classification Search
CPC ....... F16L 13/004; F16L 13/00; F16L 13/007; F16L 25/0072; F16L 33/20; F16L 33/207;
(Continued)

(56) References Cited

U.S. PATENT DOCUMENTS 3,565,116 A * 2/1971 Gabin .................... F16L 33/24
285/247
3,975,039 A * 8/1976 Penneck ................. B29C 65/68
285/133.11
(Continued)

FOREIGN PATENT DOCUMENTS

DE    197 35 261 C1    12/1998
DE    201 16 488 U1    2/2003
(Continued)

OTHER PUBLICATIONS

International Search Report, dated Feb. 1, 2016, from corresponding PCT application No. PCT/FR2015/053156.

*Primary Examiner* — Aaron M Dunwoody
(74) *Attorney, Agent, or Firm* — Nixon & Vanderhye

(57) ABSTRACT

Disclosed is a fluid connection system including a sleeve, a pipe and a fluid connector, the fluid connector including at least one rigid body made from a sterilizable biocompatible material, and the pipe including a flexible connection portion made from a sterilizable biocompatible material that is at least partially elastomeric. The fluid connector and the flexible connection portion of the pipe are assembled to one another, with the flexible connection portion of the pipe surrounding the rigid body, and the sleeve being shrunk tightly, but with free movement, on the pipe.

14 Claims, 8 Drawing Sheets

(51) Int. Cl.
  *A61M 39/00* (2006.01)
  *A61M 39/16* (2006.01)
  *A61M 39/10* (2006.01)
  *F16L 33/22* (2006.01)
  *A61M 39/12* (2006.01)
  *F16L 33/207* (2006.01)
  *F16L 33/30* (2006.01)

(52) U.S. Cl.
  CPC ........ *A61M 39/1011* (2013.01); *A61M 39/12* (2013.01); *A61M 39/16* (2013.01); *F16L 33/2071* (2013.01); *F16L 33/22* (2013.01); *F16L 33/30* (2013.01); *A61M 2039/1066* (2013.01); *A61M 2205/0216* (2013.01); *A61M 2207/00* (2013.01); *F16L 2201/44* (2013.01)

(58) Field of Classification Search
  CPC ... F16L 33/2071; F16L 33/2073; F16L 47/20; F16L 47/22; F16L 47/24
  USPC ............................................ 285/381.1–381.5
  See application file for complete search history.

(56) References Cited

U.S. PATENT DOCUMENTS

| | | | | |
|---|---|---|---|---|
| 4,169,477 A * | 10/1979 | Bokros | ................. | A61B 17/11 285/381.1 |
| 4,232,712 A * | 11/1980 | Squires | ................. | B29C 61/04 138/109 |
| 4,641,860 A * | 2/1987 | McMickle | ............ | A61M 39/12 285/133.11 |
| 4,650,228 A * | 3/1987 | McMills | ............... | B29C 61/006 156/86 |
| 4,896,904 A * | 1/1990 | Gadsden | ............. | B29C 61/0616 156/86 |
| 5,033,775 A * | 7/1991 | Matte | ................. | B29C 45/14614 285/133.11 |
| 5,338,070 A * | 8/1994 | Horikawa | ............. | F16L 13/004 285/148.23 |
| 5,411,300 A * | 5/1995 | Mitsui | ..................... | B29C 65/70 285/133.11 |
| 5,531,483 A * | 7/1996 | Christian | ............ | B29C 61/0608 156/86 |
| 5,566,988 A | 10/1996 | Johnston et al. | | |
| 5,770,139 A * | 6/1998 | Kinghorn | ............... | A61M 39/12 264/230 |
| 6,206,430 B1 * | 3/2001 | Pond | ....................... | F16L 37/08 285/3 |
| 2005/0287326 A1 | 12/2005 | Schunke et al. | | |
| 2008/0284163 A1 | 11/2008 | Proulx et al. | | |
| 2010/0254758 A1 * | 10/2010 | Campbell | ............. | F16L 13/141 403/409.1 |
| 2013/0168958 A1 * | 7/2013 | Van Den Bergh | .......................... | B29C 61/0616 285/294.1 |
| 2014/0291982 A1 * | 10/2014 | Orr | ....................... | F16L 13/141 285/257 |
| 2016/0151620 A1 | 6/2016 | Blake et al. | | |

FOREIGN PATENT DOCUMENTS

| | | |
|---|---|---|
| DE | 10 2005 024 621 A1 | 12/2006 |
| EP | 1 998 096 A2 | 12/2008 |
| FR | 1 356 350 A | 3/1964 |
| GB | 808984 A | 2/1959 |

* cited by examiner

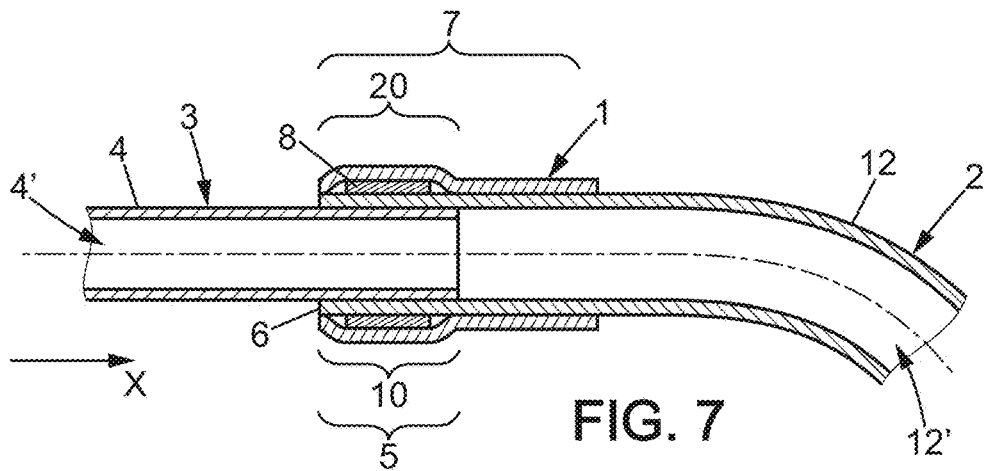
FIG. 7
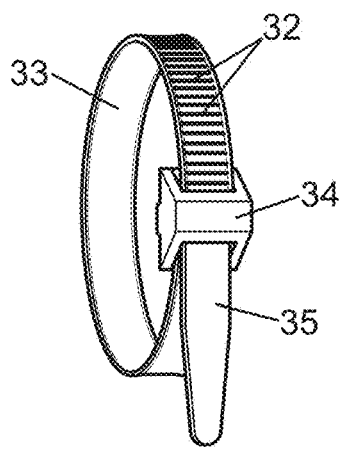
FIG. 8
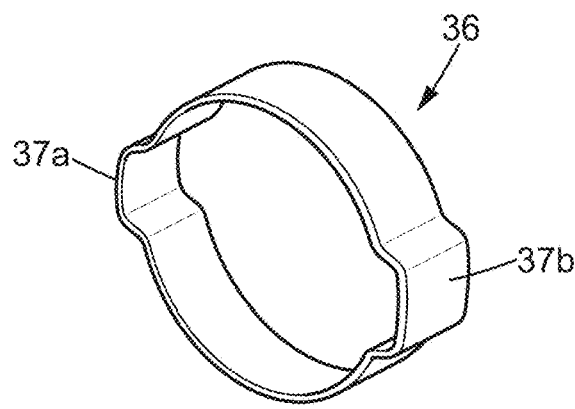
FIG. 9
FIG. 10a
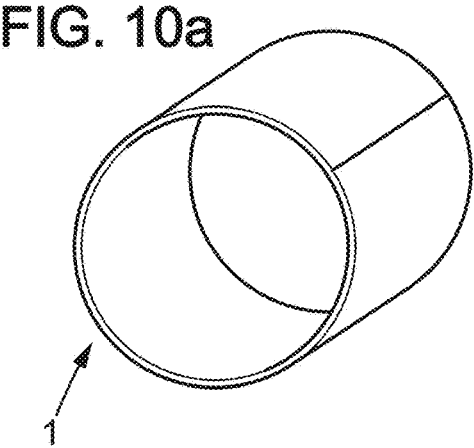
FIG. 10b
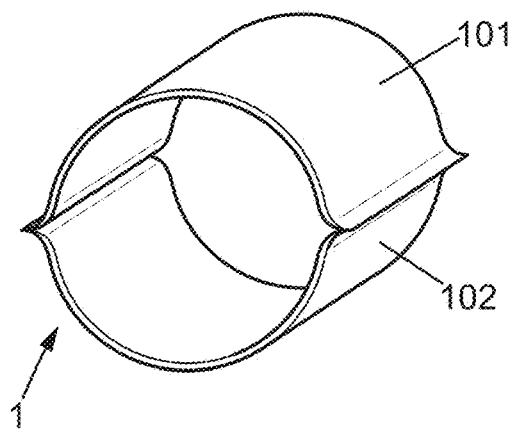

FLUID CONNECTION SYSTEM AND PRODUCTION METHOD

FIELD OF THE INVENTION

The present invention relates to fluid connection systems for the fluidtight transfer of medical and biopharmaceutical fluids, and to their manufacturing methods.

BACKGROUND OF THE INVENTION

There are already commonly known fluid connection systems for the fluidtight transfer of medical and biopharmaceutical fluids using a hose damp to retain a tube on a plastic endpiece, in patent application FR1356350. However, placement of the clamp requires mechanically clamping it on the hose and cutting off its end, which runs the risk of particulate contamination. In addition, there is the problem of tightening all clamps with uniform clamping forces from clamp to damp, due to the difficulty of automating this process. The use of such clamps also poses problems in keeping a constant tightening torque throughout the life of the product (difficult because of creep over time in the plastic material of the elements of the fluid connection system). Finally, the design of these clamps does not allow uniform clamping all along the periphery of the fluid connection. This assembly method also adversely impacts clean room productivity since the hose clamp placement, tightening, and cutting are done manually and the total technical time required is particularly long. In addition, certain constituent materials of the damp may be sources of contamination for the very clean environments (clean room, etc.) in which they are used. And finally, despite precautions, a hose clamp could damage nearby flexible pouches or tubes with a potentially damaging part of said damp.

Also commonly known is a fluid connection system for the fluidtight transfer of medical and biopharmaceutical fluids, using gripping rings. Document EP1998096 for example discloses such connections. However, these connection systems have limited resistance to fluid pressure at the connection, and there is the issue of adapting the dimensions to the use.

Also known is a fluid connection system between a connector and a hose using a thermoshrinkable sleeve, for example disclosed in document DE102005024621. This system calls for adhering the sleeve to the underlying tube or connector to attach it and to prevent the entry of foreign particles at the hose/connector connection. The use of an adhesive may be unsuitable for the underlying material, and is temperature sensitive. In addition, the use of an adhesive runs the risk of contaminating the biopharmaceutical fluid. There is also the risk of deterioration of the components in contact with the adhesive, and migration into the biopharmaceutical fluid of contaminants originating from this deterioration.

An alternative solution for the hose/connector assembly specially adapted for the biopharmaceutical field is therefore sought.

OBJECTS AND SUMMARY OF THE INVENTION

To this end, according to the invention, a fluid connection system comprises a sleeve, a hose, and a fluid connector, said fluid connector comprising at least one rigid body made of a sterilizable biocompatible material, defining a first bore, the rigid body comprising a first endpiece portion for mechanical assembly, said hose comprising a flexible connection portion made of an at least partially elastomeric sterilizable biocompatible material, defining a second bore and an end, the flexible connection portion comprising a second portion for mechanical assembly, the fluid connector and the flexible connection portion of the hose being assembled to one another by mechanical engagement in an assembly region of the first endpiece portion and second endpiece portion for mechanical assembly, in an assembly configuration in which the flexible connection portion of the hose surrounds the rigid body, and the first and second bores are in fluid communication with each other, said sleeve being shrunk to be tight but with free movement on the hose and extending over a predetermined stiffening region extending over at least a portion of the assembly region.

In the case of such a connection system, no adhesive is required between the elements to be assembled, which reduces the risk of contamination. With such a connection system, the tightening of the hose and the connector onto one another compensates for manufacturing tolerances in the connector and hose, which improves the seal and the mechanical strength. In addition, the sleeve eliminates the risk of separation between the connector and hose, related to the increase in pressure inside the hose which can lead to leaks in the assembly region between the hose and connector.

In various embodiments of the connection system according to the invention, one or more of the following arrangements may possibly be used:

- the stiffening region extends from the hose end,
- the first endpiece portion for mechanical assembly of the fluid connector comprises at least one catch projecting radially outward, the second portion for mechanical assembly of the hose being positioned above said at least one catch during assembly of the fluid connector and the flexible connection portion of the hose, said catch being adapted to retain the hose around the rigid body,
- said catch is adapted to ensure proper retention of the hose when tensile force is applied,
- the at least one catch is molded in the radially outer surface of the fluid connector,
- the first endpiece portion for mechanical assembly of the fluid connector comprises a stop, said stop forming an axial stop surface for the second portion for mechanical assembly in the assembly configuration and a front surface opposite to the stop surface,
- the sleeve covers the stop, bearing against the front surface of said stop.

This allows for better retention of the sleeve.

- the sleeve extends from the hose end and along a portion of the hose beyond the assembly region, For a long sleeve which encloses the entire assembly region, it prevents the flexible hose from swelling near the assembly region, as such swelling can result in leaks.

- the sleeve extends from the hose end and along a portion of the hose strictly within the assembly region,
- the sleeve extends between the hose end and the catch,
- the components are rotationally symmetrical,
- the sleeve is created as one piece with no predetermined breaking point, the sleeve is the sole means of stiffening the hose on the fluid connector, a hose clamp is tightened onto the hose in the assembly region before placement of the sleeve.

In addition, in the possible case where a hose clamp is used at the assembly between the hose and connector to ensure better retention of the assembly and a better seal, a sleeve provided around the assembly and hose clamp will protect the environment against possible contamination of the environment by material from the clamp and will prevent the geometry of the clamp from damaging other components in the environment.

The invention further relates to a method for manufacturing a fluid connection system between a hose and a fluid connector, said fluid connector comprising at least one rigid body made of a sterilizable biocompatible material, defining a first bore, the rigid body comprising a first endpiece portion for mechanical assembly, said hose comprising a flexible connection portion made of an at least partially elastomeric sterilizable biocompatible material, defining a second bore and an end, the flexible connection portion comprising a second portion for mechanical assembly, the method comprising the following two steps carried out in any order:

the fluid connector and the flexible connection portion of the hose are assembled to one another by mechanical engagement in an assembly region of the first and second portions for mechanical assembly, in an assembly configuration in which the flexible portion of the hose surrounds the rigid body, over an assembly region, the first and second bores being in fluid communication with each other, a sleeve is positioned loosely around the hose, said sleeve being of thermoshrinkable material, said sleeve extending over a predetermined stiffening region extending over at least a portion of the assembly region;

the method then comprising the following step:

said sleeve is shrunk to be tight but with free movement on the hose, extending over a predetermined stiffening region extending over at least a portion of the assembly region.

In one embodiment of the method of the invention, the following provision may possibly also be used:

the sleeve is shrunk by applying a temperature of more than 80° for longer than 3 seconds at the sleeve.

With no need for cutting a hose clamp and with no sharp edges, particulate contamination is reduced and the risk of protruding areas causing perforation damage to pouches is reduced.

In addition, as shrinkage of the sleeve 1 onto the hose 2 can be carried out with an automated machine, possibly in parallel with other steps, productivity is improved.

Other features and advantages of the invention will be apparent from the following description of one of its embodiments, given by way of non-limiting example, with reference to the accompanying drawings.

BRIEF DESCRIPTION OF THE DRAWINGS

In the drawings:

FIG. 7 is a representation of the fluid connection system when a hose clamp is used prior to assembly, FIG. 8 illustrates a plastic hose clamp, FIG. 9 illustrates a metal hose clamp, FIGS. 10a-b are a representation of alternative geometries of the sleeve.

In the various figures, the same references designate identical or similar elements.

MORE DETAILED DESCRIPTION

Figure 1:
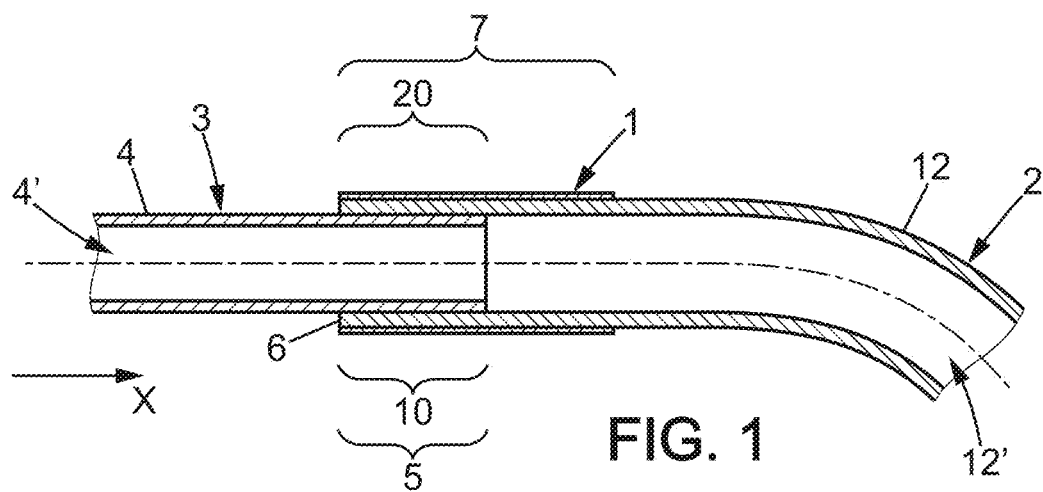
FIG. 1 is a representation of the fluid connection system.

FIG. 1 shows a fluid connection system comprising a sleeve 1 that encloses the assembly between a hose 2 and a connector 3 (partially represented). The fluid connection system is intended for the transfer of biopharmaceutical fluid.

In the context of the invention, the term "biopharmaceutical fluid" is understood to mean a fluid derived from biotechnology—culture media, cell cultures, buffer solutions, artificial nutrition liquids, blood components and blood products derived therefrom, or a pharmaceutical fluid, or more generally a fluid for use in the medical field. Such fluids preferably have high purity requirements and must not be contaminated with foreign particles, whether these are particles from devices in contact with the fluids for their containment, transportation, or processing, or particles from the atmosphere surrounding these devices.

In the current example, in the final configuration of the system the sleeve 1 extends in the longitudinal direction X of assembly, around the hose 2 and the connector 3.

The sleeve 1 is positioned in an initial configuration around the assembly between the hose 2 and the connector 3, and then shrunk to enclose the assembly. The sleeve extends over a stiffening region 7. The shrinking consists of reducing the inside diameter of the sleeve 1, which is concurrent for example with a decrease in the outside diameter thereof. Thermoshrinking is performed for example, in which the application of heat or cold to the sleeve 1 results in this decrease. In particular, such application leads to a decrease in the inside diameter of the sleeve to be greater than that of the outside diameter of the underlying components. This decrease in the inside diameter of the sleeve 1 thus takes place while the hose 2 and connector 3 remain assembled together.

The sleeve 1 is shrunk to be tight but with free movement on the hose 2. This assembly with free movement is such that the thermoshrunk sleeve 1 remains movable on the underlying hose 2 if the friction force between the sleeve 1 and the hose 2 is overcome. In practice, it is not otherwise attached to the assembly aside from the friction, but is not movable. The friction force between the sleeve and hose 2 is greater than another force that would disassemble the system, for example the force to detach the hose 2 and connector 3.

The permitted pressure when using this type of connection assembly after tightening the sleeve can reach 3 bars inside the hose 2.

As illustrated in FIG. 1, the sleeve 1 has for example a generally cylindrical shape along the axis X. The sleeve 1 comprises a hollow elongated body.

As illustrated in FIG. 1, the fluid connector 3 comprises at least one rigid body 4, said body defining a first bore 4'. The body of the connector 3 comprises a first endpiece portion for mechanical assembly 10.

As illustrated in FIG. 1, the hose 2 comprises a flexible connection portion 12 defining a second bore 12' and an end 6. The flexible connection portion comprises a second mechanical assembly portion 20.

The rigid body 4 of the fluid connector 3 is made of a sterilizable biocompatible material. The rigid body is for example of plastic, polyethylene (PET), polypropylene (PP), polycarbonate, polyethersulfone (PES), or other suitable material.

The flexible connection portion of the hose 2 is deformable. The flexible portion is made of a sterilizable biocompatible material, at least partially elastomeric, for example TPE or silicone. The hose 2 may be created to be flexible, which facilitates for example the connection of two containers using the hose. In addition, the flexible connection portion can be deformed for assembly to the rigid body 4. The outside diameter of the hose 2 is for example not more than 4 cm.

As also illustrated in FIG. 1, the fluid connector 3 and the flexible connection portion of the hose 2 are assembled together by mechanical engagement (friction) in an assembly region 5 of the first 10 and second 20 portions for mechanical assembly. In this assembly configuration, the flexible portion 12 of the hose 2 surrounds the rigid body 4 and is in close contact therewith. The first and second bores 4', 12', are in fluid communication with each other.

The assembly may be achieved for example by forced insertion of the flexible portion 12 of the hose 2 around the rigid body 4, the bore of the hose 2 and the bore of the connector 3 then being in fluid communication. This single forced insertion may be sufficient to hold the hose 2 and connector 3 together, at least when there is no flow through the connector 3 and/or no significant mechanical stress on the connector/hose assembly.

The connector 3 may for example be a hollow rigid body having two ends: one end comprised within the first endpiece portion for mechanical assembly 10, and a second opposite end. The two opposite ends are in fluid communication with each other. The connector 3 is for example molded as one piece.

Figure 2:
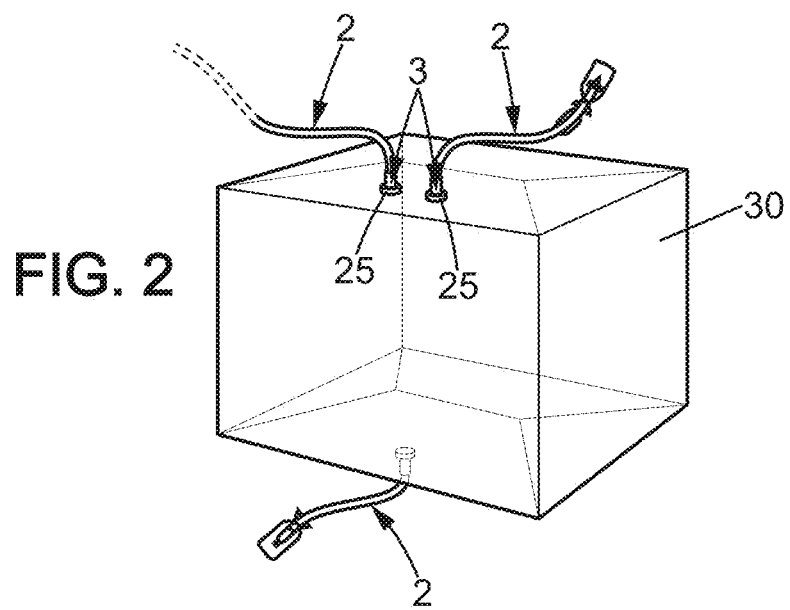
FIG. 2 is a representation of a connector mounted between a hose and a pouch.

The connector 3 is for example assembled to a container 30 of biopharmaceutical product so as to allow fluid communication with the interior thereof, as illustrated in FIG. 2. The container 30 is for example a flexible pouch. The connector 3 is for example welded to a pouch by its second end, for example by a portion 25 of the rigid body 4 other than the first endpiece portion for mechanical assembly 10, so that the inside of the pouch is in fluid communication with the bore 4'.

The second end may also be integrated with a multi-connector in the shape of a Y, T, etc., to provide a connection between hoses, or may be integrated with a clip-on connector, male or female, to provide a connection of pouch to hose or hose to hose.

Figure 3A:
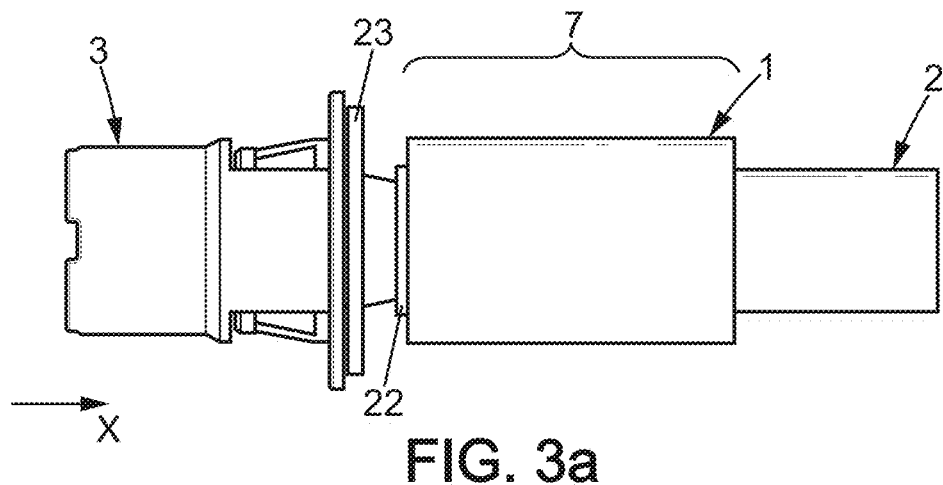
FIGS. 3a-d are a representation of the fluid connection system when the sleeve covers the entire assembly portion, before and after shrinking.

The connector 3 may also include a flange 23 (FIG. 3a). Said flange 23 is for example provided at the outer surface of the connector 3. It extends radially along the circumference of the connector 3. It comprises a side facing the hose 2 and an opposite side in the longitudinal direction X. Its side opposite to the side facing the hose may serve as a support for insertion, abutting against another element on the connector 3 on the side opposite to the connector 3/hose 2 assembly in the longitudinal direction X.

The thermoshrinkable sleeve 1 may be for example of polyethylene terephthalate (PET), polypropylene (PP), ethylene tetrafluoroethylene (ETFE).

The entire assembly described above is preferably rotationally symmetrical.

In a first embodiment, illustrated in FIGS. 3a-d, the first 10 and second 20 portions for mechanical assembly overlap in the assembly region 5.

The first endpiece portion for mechanical assembly 10 of the fluid connector 3 comprises at least one catch 21. The catch 21 is for example provided on the surface of the first endpiece portion for mechanical assembly 10 of the fluid connector 3, over the entire circumference of the connector for example, thus not defining areas of concentrated stress. The catch 21 could also be provided on only a portion of the circumference.

Several catches, for example (regularly) spaced along the axial direction, may be provided for example on the surface of the first endpiece portion for mechanical assembly 10.

During assembly of the fluid connector 3 and the flexible connection portion 12 of the hose 2, the hose 2 surrounds the rigid body 4 and the second portion for mechanical assembly 20 of the hose 2 is placed above said at least one catch 21: the hose 2 then has a retaining inside diameter that is greater than the inside diameter of the unmounted hose 2. This deformation guarantees a certain tightening of the hose 2 on the connector 3. This configuration is called the "assembly configuration" of the hose 2 and connector 3.

The catch 21 retains the hose 2 when tensile force is applied to the hose 2 along its longitudinal axis X.

Biocompatible coatings on the radially outer surface of the first endpiece portion for mechanical assembly 10 may be used to increase adhesion of the surface of the connector 3 to the hose 2 when tensile force is applied.

The connector 3 may, for example, also include a stop ring 22 which serves as a stop for insertion of the hose 2 onto the rigid body 4, during assembly of the fluid connector 3 and the flexible portion 12 of the hose 2.

The stop 22 may for example be provided on the surface of the rigid body 4.

Figure 3B:
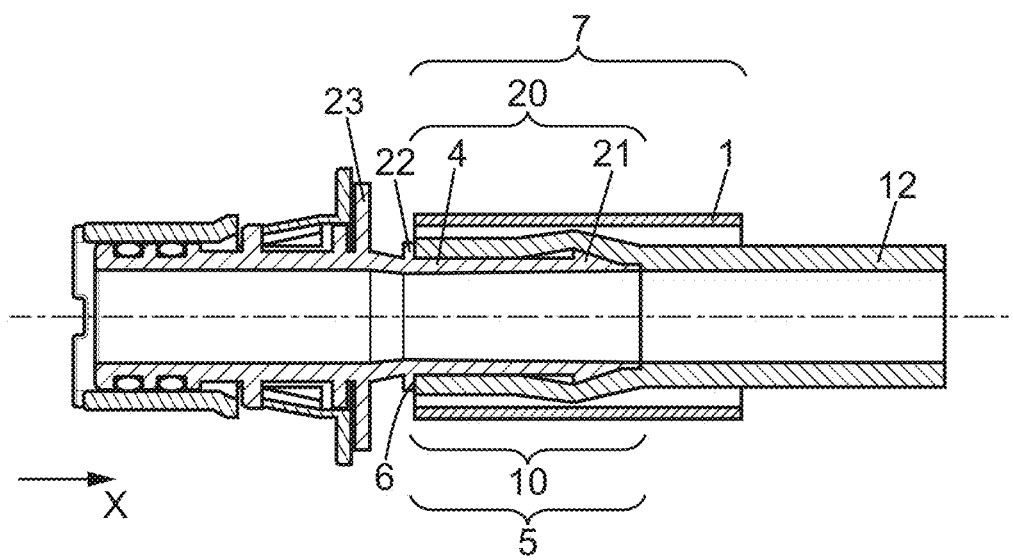

The sleeve 1 is then positioned loosely around the assembly region 5 as shown in FIGS. 3a and 3b. In this embodiment, said sleeve 1 extends over a stiffening region 7 provided from the end 6 of the hose 2 and beyond the assembly region 5 on the hose 2.

Alternatively, the stiffening region 7 may extend continuously over a portion of the connector 3 upstream of the assembly region 5 then into the assembly region 5 and beyond the assembly region 5 on the hose 2 in the longitudinal direction X (not shown).

Figure 3C:
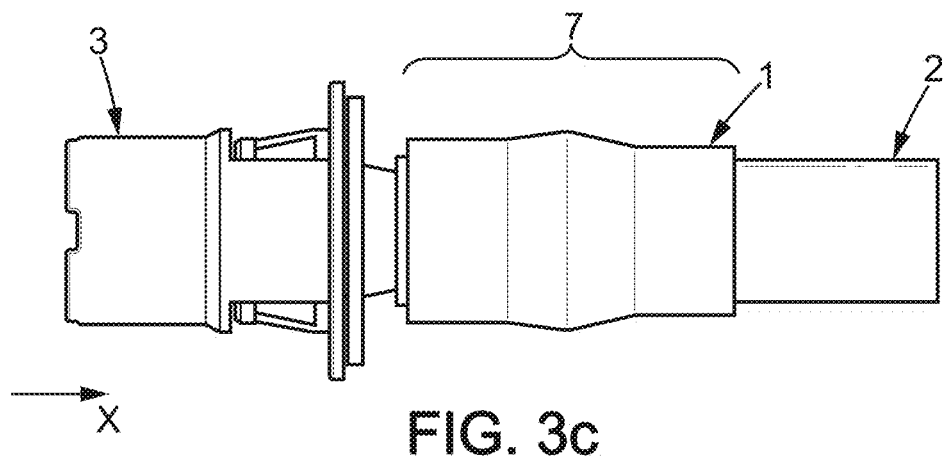
Figure 3D:
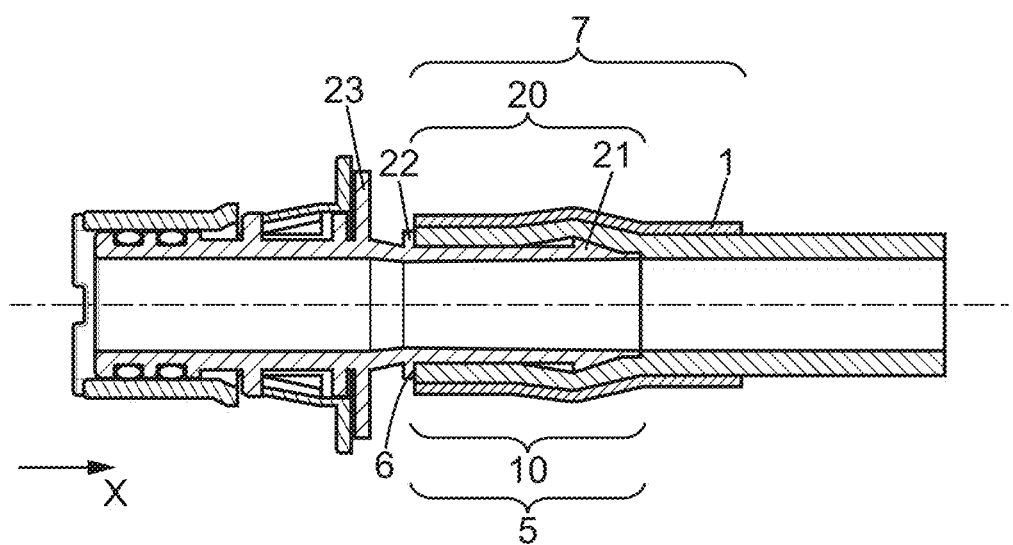

The thermoshrinkable sleeve 1 has an inside diameter that is greater than the outside diameter of the hose 2 in the assembled configuration, to enable such assembly. The sleeve 1 has the ability to shrink onto the hose when heated in order to retain the hose on the connector as shown in FIGS. 3c and 3d.

Figure 4:
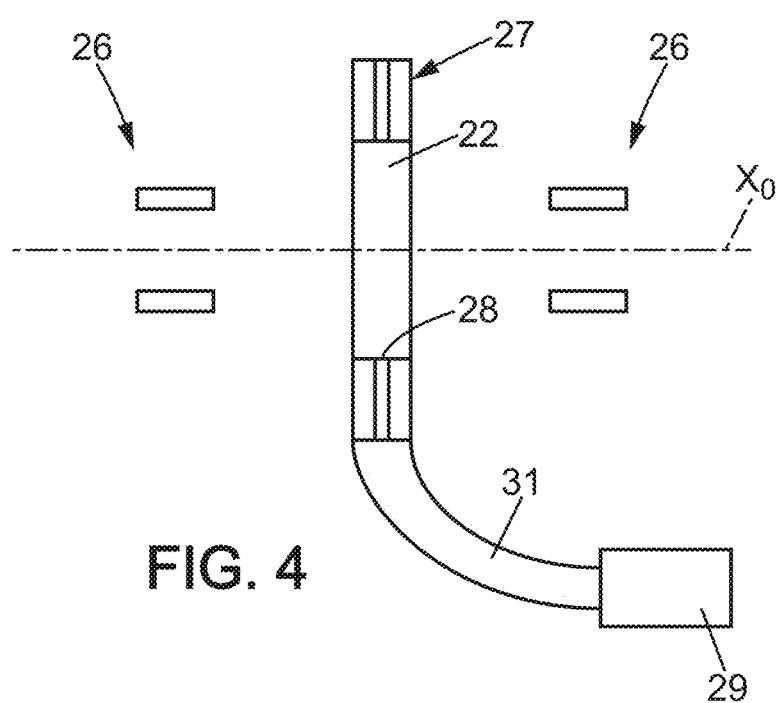
FIG. 4 shows an example of a production facility.
Figure 5A:
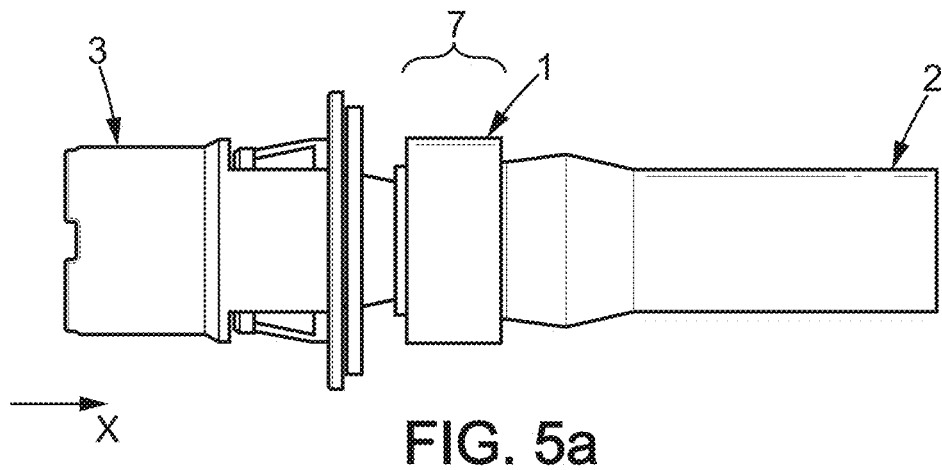
FIGS. 5a-d are a representation of the fluid connection system when the sleeve partially covers the assembly portion, before and after shrinking.
Figure 5B:
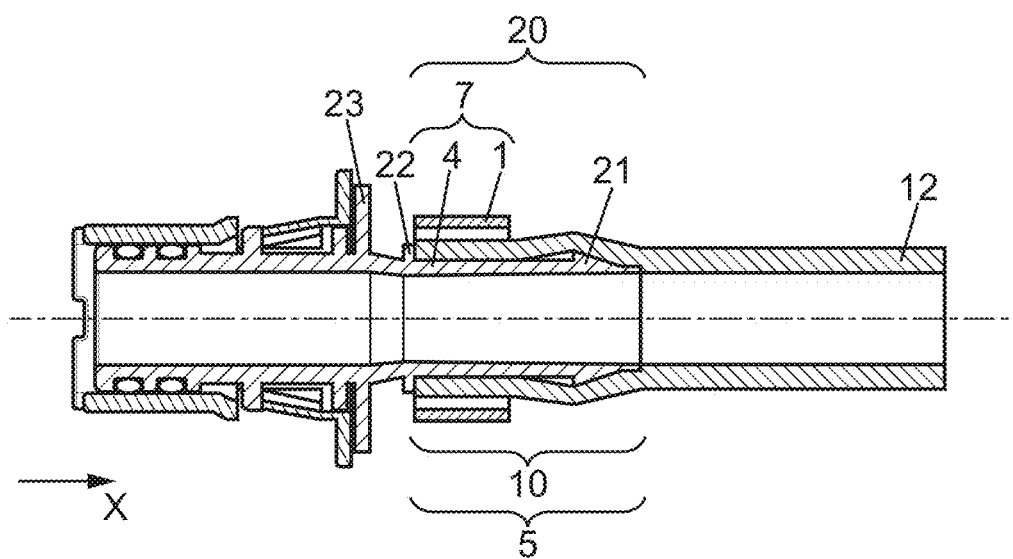
Figure 5C:
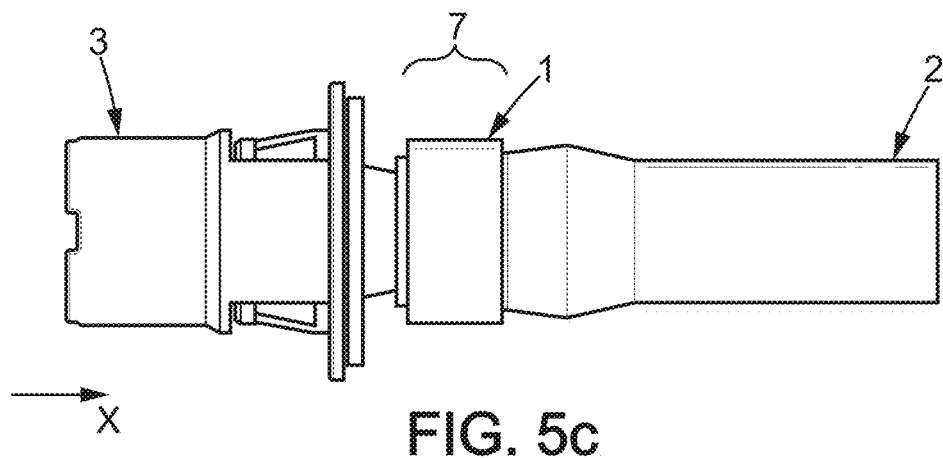
Figure 5D:
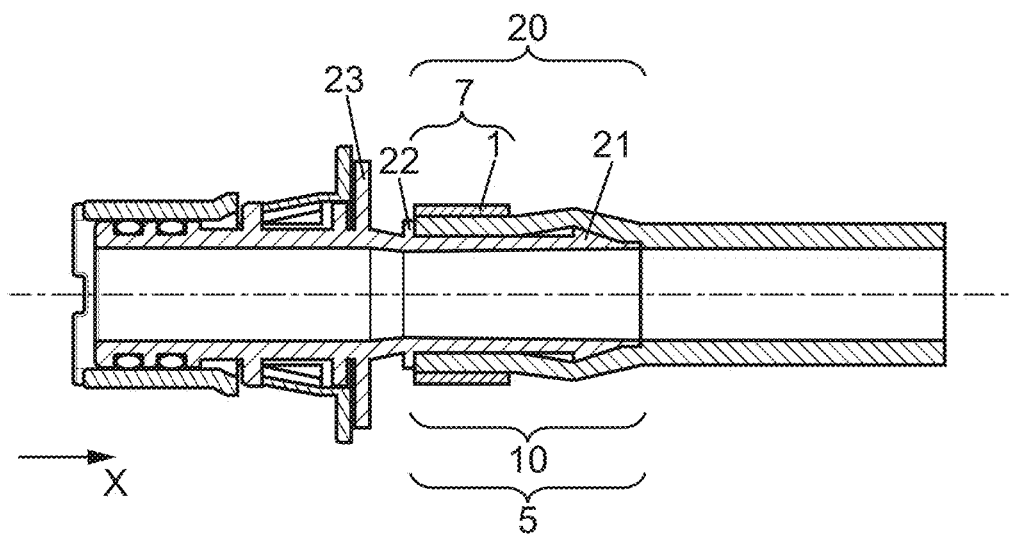

The sleeve may be heated by hot air. Such heating may then be done for example using one or more nozzle(s) which blow a stream of hot gas (for example air) around the sleeve 1. FIG. 4 shows an illustrative example of one embodiment. A gripping system 26 is used to position the assembly region 5 at the relevant location in the production facility. This system is for example a clamp holding the connector 3 and a clamp holding the hose 2, arranged so that the assembly region 5 is centered about an assembly station axis $X_0$. A support 27 surrounds axis $X_0$ and carries a plurality of blowing nozzles 28 arranged circumferentially about axis $X_0$. The nozzles 28 are connected to a source 29 of hot gas by means of appropriate piping 31. Such a method can be carried out in a short period relative to the time required for the assembly of such fluid connection systems, for example a period of less than 1 minute, to reach a shrinking temperature above 80° C. at the sleeve.

The sleeve could also be heated by bringing a heating element close to the sleeve. The heating time can range from 3 seconds to 30 seconds at temperatures from 80° C. to 350° C. depending on the distance between the heating element and the sleeve 1. For example, a hot annular element surrounding axis $X_0$ is used.

The method enables shrinking the sleeve onto the hose 2 within a few seconds for example. The diameter of the sleeve 1 would for example shrink by 50% with the present method when there are no underlying components.

In another variant, the heat may be provided by thermal welding (non-contact infrared). In such a method, the radiation source may be arranged around the sleeve 1 at a distance therefrom, or extend axially for a limited distance and be moved axially back and forth along the sleeve (along axis $X_0$). This also applies to the other methods described above.

Alternatively, the heat may be provided by dipping in a hot liquid (for example water).

The sleeve 1 could also be elastically stretched to increase its diameter, prior to its mounting on the assembly, in order to increase the retention force. The sleeve 1 is stretched for example and placed on the hose 2 over the assembly region 5. The hose 2 and connector 3 are then assembled, and the sleeve 1 released so that it elastically clamps the hose 2. The sleeve 1 accepts the increase in diameter of the hose 2 resulting from its assembly on the connector.

In the case of a rotationally symmetrical system, the 360° clamping of the hose 2 compensates for manufacturing tolerances of the connector 3 and hose 2, which improves the seal and mechanical strength.

The catch 21 also retains the sleeve 1 in position in the longitudinal direction X.

Once tightened, the sleeve 1 applies 360° of radial pressure on the hose 2, to seal the interface between the fluid connector 3 and the hose 2 under pressure. During the passage of a biopharmaceutical fluid, possibly under pressure, between the flexible hose and the connector, the sleeve rigidly maintains the connection between the flexible hose and the connector, thereby reducing the risk of hose deformation at the interface with the connector and consequently the chance of a leak.

By applying thermal activation of the sleeve 1 in a controlled manner, the hose 2 is thus uniformly stiffened in the stiffening region 7 over the periphery of the hose.

The sleeve 1 follows the shape of the assembly that it covers, in the area it covers.

In one embodiment, illustrated in FIGS. 5a-5d, the sleeve 1 is shorter than the assembly region 5. The sleeve 1 extends over a stiffening region 7 provided from the end of hose 2 and over a portion of the assembly region 5 in the longitudinal direction X.

Alternatively, in the case where the surface of the first endpiece portion for mechanical assembly 10 comprises both a catch 21 and a stop 22, the sleeve 1 may be placed axially between the stop 22 and the catch 21.

Alternatively, the stiffening region 7 may extend continuously over a portion of the connector 3 upstream of the assembly region 5 then over a portion of the assembly region 5 in the longitudinal direction X (not shown).

Figure 6A:
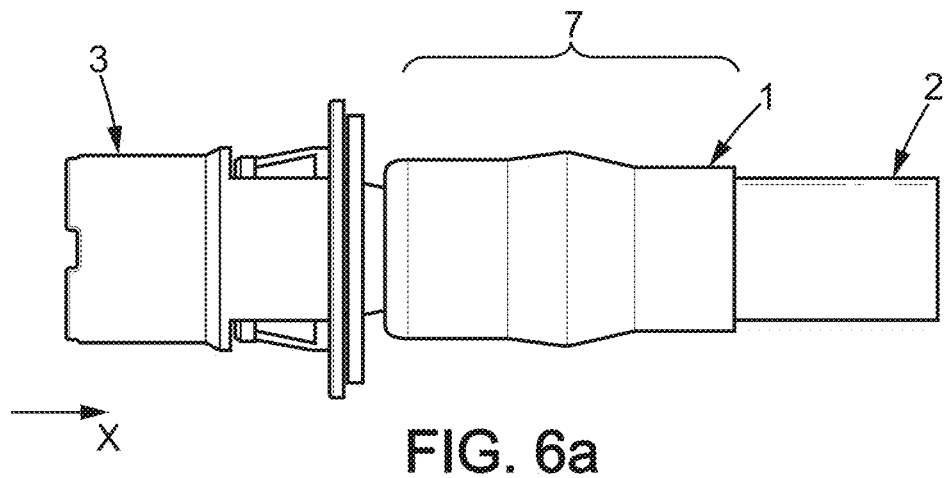
FIGS. 6a-b are a representation of the fluid connection system with a sleeve retaining rib.
Figure 6B:
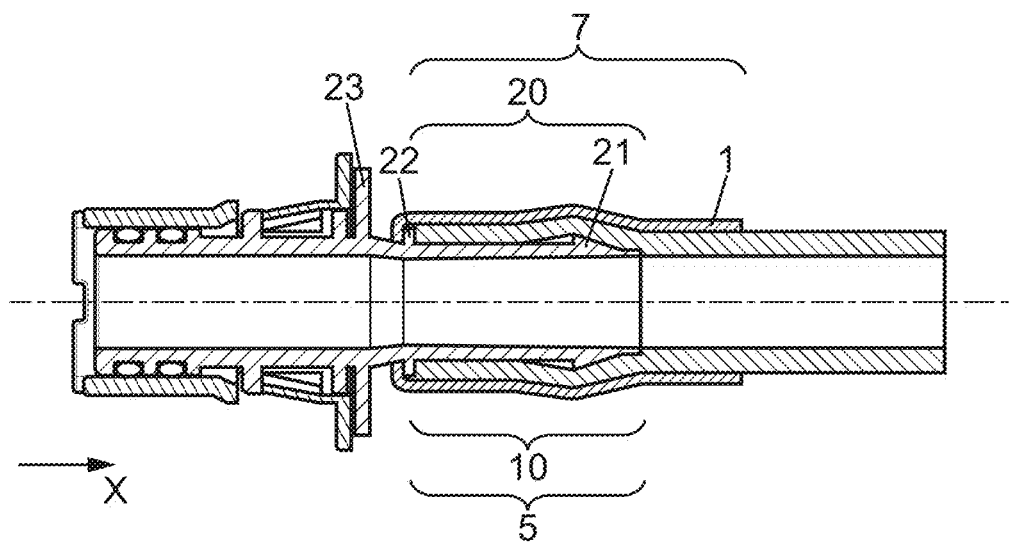

In another embodiment, shown in FIGS. 6a-6b, the sleeve 1 shrinks and grips the stop 22 of the first endpiece portion for mechanical assembly 10, the sleeve enclosing the stop 22 in order to better encapsulate the assembly of the fluid connector 3 with the flexible connection portion 12 of the hose 2. In the example presented, the sleeve 1 shrinks to fit tightly onto the face of the stop 22 opposite the face receiving the hose 2.

In another embodiment, shown in FIG. 7, a hose clamp 8 is mounted beforehand on the previously described assembly of the connector 3 and hose 2. The thermoshrinkable sleeve 1 is then positioned on the previously described assembly, to surround the assembly and the hose clamp 8, and is shrunk. The sleeve 1 then snugly fits to the shape of the clamping collar 8 at the assembly.

A plastic hose clamp may be used for example, of Rilsan® polyamide for example. This type of plastic clamp, shown in FIG. 8, comprises a system of catches 32 on a strip 33 which engage with a locking hook arranged in the head 34, such that the clamping is not reversible. In other words, once the strip 33 is engaged with the head 34 to form a loop, one pulls on the strip 33 to reduce the diameter of the loop and tighten the hose clamp 8, the locking hook engaging with one of the catches 32 of the strip 33 to prevent loosening. Once tightened, to prevent the strip from extending too far beyond the diameter of the hose clamp loop, the free portion of the strip is cut near the head of the clamp. The remaining undetached portion 35 of the strip often has a sharp edge which can cut.

Alternatively, one may also use a metal clamp such as a crimpable ring, illustrated in FIG. 9, which is in the form of a preformed ring 36 provided having one or two ears 37a, 37b projecting outward relative to the general shape of the ring, this type of clamp being sold by the company Oetiker®. After insertion of the clamp onto the tube to be retained, a tool is used to crimp the ear (or ears) of the clamp which causes permanent deformation and thus narrows the main diameter of the ring and therefore tightens the clamp on the tube. This type of clamping with a metal ring is particularly robust and reliable. However, at the point where the ear is crimped by the tool, there may be roughness or a burr forming a sharp edge that could cause damage.

The addition of the sleeve 1 to the assembly prevents any protruding portion of the clamp from piercing adjacent pouches for example during transportation or even from injuring the user. The clamp is wrapped in the sleeve 1 which smoothes the protruding ends. In addition, a metal clamp can advantageously be covered to prevent contamination of the clean environment in which it would be used, such as a clean room.

The sleeve 1 is preferably rotationally symmetrical, as shown in FIG. 10a. Alternatively, the sleeve 1 may be in the form of two half rings 101 and 102 joined by their respective ends as illustrated in FIG. 10b. In the case of such a sleeve, the two half rings 101 and 102 are for example fixed together by their respective free ends, and each joining of assembled free ends is flattened so that said joining of assembled free ends protrudes radially outward from the sleeve 1.

Alternatively, the sleeve 1 is mounted on the hose 2 before the hose 2 is mounted on the first endpiece portion for mechanical assembly 10 of the connector 3.

In another variant, the hose 2 is mounted on the first endpiece portion for mechanical assembly 10 of the connector 3, then the sleeve is mounted on the hose 2 for example by sliding the sleeve 1 onto the preceding assembly.

Alternatively, the sleeve 1 has at least one incision along its entire length, along X, for placing the sleeve around the assembly after the hose 2 and connector 3 are assembled together.

The invention claimed is:

1. A fluid connection system for transferring biopharmaceutical fluid, the fluid connection system comprising:
   a sleeve of thermo-shrinkable material,
   a plastic hose, and
   a fluid connector,
   wherein the fluid connector comprises a single-piece rigid body made of a sterilizable biocompatible material, defining a first bore, the single-piece rigid body comprising a first endpiece portion for mechanical assembly, which is a male portion,
   wherein the hose is a single-piece hose comprising a flexible connection portion made of at least partially elastomeric sterilizable biocompatible material, defining a second bore and an annular end, the flexible connection portion comprising a second endpiece portion for mechanical assembly,
   the fluid connector and the flexible connection portion of the hose being assembled to one another by mechanical engagement in an assembly region of the first endpiece portion and second endpiece portion for mechanical assembly, in an assembly configuration in which the flexible connection portion of the hose surrounds the rigid body, and the first and second bores are in fluid communication with each other, the single-piece rigid body being in contact only with the flexible connection portion of the hose in the assembly region,
   the sleeve being shrunk to be tight but with free movement on the hose and extending over a provided stiffening region extending from the annular end of the hose and beyond the assembly region on the hose,
   the sleeve extending from the annular end of the hose and along a portion of the hose beyond the assembly region, so as no other component is provided between the flexible connection portion of the hose and the single-piece rigid body, and
   wherein the sleeve is the sole means of stiffening the hose on the fluid connector, so that the male portion, which is made of a single-piece, is only surrounded by two pieces, which are the hose and the sleeve.

2. The fluid connection system according to claim 1, wherein the first endpiece portion for mechanical assembly of the fluid connector is a male portion that comprises:
   a front subpart provided with at least one catch projecting radially outward, the front subpart including a free end of the male portion,
   a rear subpart without any catch projecting radially outward, and
   wherein the second portion for mechanical assembly of the hose is directly covering the front subpart and the rear subpart during assembly of the fluid connector and the flexible connection portion of the hose, said at least one catch being adapted to retain the hose around the rigid body.

3. The fluid connection system according to claim 2, wherein the male portion extends frontward from a stop ring arranged away from the at least one catch projecting radially outward, the front subpart and the rear subpart forming the male portion, the rear subpart longitudinally extending between the stop ring and the front subpart.

4. The fluid connection system according to claim 2, wherein the at least one catch is molded in the radially outer surface of the fluid connector.

5. The fluid connection system according to claim 1, wherein the first endpiece portion for mechanical assembly of the fluid connector comprises a stop, said stop forming an axial stop surface for the second portion for mechanical assembly in the assembly configuration and a front surface opposite to the stop surface.

6. The fluid connection system according to claim 5, wherein the sleeve covers the stop, bearing against the front surface of said stop.

7. The fluid connection system according to claim 1, wherein the components are rotationally symmetrical.

8. The fluid connection system according to claim 1, wherein the sleeve is created as one piece with no predetermined breaking point.

9. The fluid connection system according to claim 1, wherein the front subpart is provided with only one catch projecting radially outward.

10. A method for manufacturing a fluid connection system between a plastic hose for transferring biopharmaceutical fluid and a fluid connector made of plastic, said fluid connector comprising a single-piece rigid body made of a sterilizable biocompatible material, defining a first bore, the rigid body comprising a first endpiece portion for mechanical assembly, which is a male portion, said hose being a single-piece hose comprising a flexible connection portion of an at least partially elastomeric sterilizable biocompatible material, defining a second bore and an annular end, the flexible connection portion comprising a second portion for mechanical assembly,
    the method comprising the following two steps carried out in any order:
    assembling the fluid connector and the flexible connection portion of the hose to one another by mechanical engagement in an assembly region of the first and second portions for mechanical assembly, in an assembly configuration in which the flexible connection portion of the hose surrounds the rigid body, over an assembly region, the first and second bores being in fluid communication with each other, wherein no other component is provided between the flexible connection portion of the hose and the single-piece rigid body and wherein the sleeve is the sole means of stiffening the hose on the fluid connector, so that the male portion, which is made of a single-piece, is only surrounded by two pieces, which are the hose and the sleeve, the single-piece rigid body being in contact only with the flexible connection portion of the hose in the assembly region, and
    placing the sleeve in a ready-to-be-shrunk position around the hose, said sleeve being of thermo-shrinkable material, said sleeve extending over a predetermined stiffening region, said stiffening region extending from the annular end of the hose and beyond the assembly region on the hose,
    the method then comprising the following step:
    shrinking said sleeve to be tight but with free movement on the hose, without any intermediary element between the sleeve and the hose, the sleeve extending over the predetermined stiffening region, the sleeve extending from the annular end of the hose and along a portion of the hose beyond the assembly region.

11. The manufacturing method according to claim 10, wherein the sleeve is shrunk by applying a temperature of more than 80° C. for longer than 3 seconds at the sleeve.

12. The manufacturing method according to claim 10, wherein the fluid connector and the flexible connection portion of the hose are assembled to one another by inserting the male portion inside the hose, the male portion being provided with:

a front subpart provided with at least one catch projecting radially outward, the front subpart including a free end of the male portion, a rear subpart without any catch projecting radially outward, and wherein the sleeve is shrunk on the hose around each of the front subpart and the rear subpart, so as to form an annular bulge in the sleeve around the at least one catch, due to local deformation of the hose radially outward around the at least one catch.

13. The manufacturing method according to claim 11, wherein the male portion extends from a stop ring and is provided with at least one catch projecting radially outward, the sleeve being shrunk so that the hose and the sleeve taper each from a bulged region around the at least one catch toward the stop ring.

14. A fluid connection system for transferring biopharmaceutical fluid, the fluid connection system comprising:

a sleeve, a plastic hose, and a fluid connector, wherein the fluid connector comprises a single-piece rigid body made of a sterilizable biocompatible material, defining a first bore, the single-piece rigid body comprising a first endpiece portion for mechanical assembly, which is a male portion, wherein the hose is a single-piece hose comprising a flexible connection portion made of at least partially elastomeric sterilizable biocompatible material, defining a second bore and an annular end, the flexible connection portion comprising a second endpiece portion for mechanical assembly, the fluid connector and the flexible connection portion of the hose being assembled to one another by mechanical engagement in an assembly region of the first endpiece portion and second endpiece portion for mechanical assembly, in an assembly configuration in which the flexible connection portion of the hose surrounds the rigid body, and the first and second bores are in fluid communication with each other, the single-piece rigid body being in contact only with the flexible connection portion of the hose in the assembly region, the sleeve being shrunk to be tight but with free movement on the hose and extending over a provided stiffening region extending from the annular end of the hose and beyond the assembly region on the hose, the sleeve extending from the annular end of the hose and along a portion of the hose beyond the assembly region, so as no other component is provided between the flexible connection portion of the hose and the single-piece rigid body and wherein the sleeve is the sole means of stiffening the hose on the fluid connector, so that the male portion, which is made of a single-piece, is only surrounded by two pieces, which are the hose and the sleeve, and wherein:

the sleeve is made of polypropylene or ethylene tetrafluoroethylene, the rigid body is made of polypropylene, or polycarbonate, polyethersulfone, and the hose is made of silicone.

* * * * *